United States Patent
Oberndorfer et al.

(10) Patent No.: US 9,494,613 B2
(45) Date of Patent: Nov. 15, 2016

(54) MODULAR FLOW INJECTION ANALYSIS SYSTEM

(75) Inventors: Christian Oberndorfer, Schwaebisch Hall (DE); Michael Winkler, Weissbach (DE); Marco Zuern, Schoental-Winzenhofen (DE)

(73) Assignee: BUERKERT WERKE GMBH, Ingelfingen (DE)

( * ) Notice: Subject to any disclaimer, the term of this patent is extended or adjusted under 35 U.S.C. 154(b) by 1141 days.

(21) Appl. No.: 13/375,968

(22) PCT Filed: May 18, 2010

(86) PCT No.: PCT/EP2010/003032
§ 371 (c)(1),
(2), (4) Date: Feb. 13, 2012

(87) PCT Pub. No.: WO2010/139398
PCT Pub. Date: Dec. 9, 2010

(65) Prior Publication Data
US 2012/0136491 A1 May 31, 2012

(30) Foreign Application Priority Data

Jun. 4, 2009 (DE) .................. 20 2009 007 800 U (51) Int. Cl.
*G05D 7/00* (2006.01)
*G01N 35/08* (2006.01)
(Continued)

(52) U.S. Cl.
CPC ........... *G01N 35/085* (2013.01); *B01F 5/0646* (2013.01); *B01F 5/0647* (2013.01); *B01F 13/0059* (2013.01); *B01L 3/502715* (2013.01); *G01N 35/1097* (2013.01);
(Continued)

(58) Field of Classification Search
None
See application file for complete search history.

(56) References Cited

U.S. PATENT DOCUMENTS 5,223,224 A * 6/1993 Dremel et al. .................. 422/81
5,250,263 A * 10/1993 Manz .............................. 422/81
(Continued)

FOREIGN PATENT DOCUMENTS

CN 1732044 A 2/2008
DE 297 03 788 6/1997
(Continued)

OTHER PUBLICATIONS

Written Opinion of the International Searching Authority re PCT/EP2010/003032, Dec. 16, 2011.
(Continued)

*Primary Examiner* — Kenneth M Lo
*Assistant Examiner* — Derrick Boateng
(74) *Attorney, Agent, or Firm* — Cowan, Liebowitz & Latman, P.C.; Steven D. Underwood (57) ABSTRACT

A modular flow injection analysis system has a sample connection, a reagent inflow and a media discharge. The analysis system is formed of a plurality of functional modules stacked one on top of the other. These functional modules include a metering module including a metering channel having an inlet and an outlet, a mixing module including a mixing channel having an inlet and an outlet, an analysis module including a media chamber connected to the outlet of the mixing channel, and a media control module. The modules are connected by aligned media channels. These media channels replace the conventional tube connections. They are connected automatically when the modules are fitted together.

18 Claims, 6 Drawing Sheets

(51) Int. Cl.
- *B01F 5/06* (2006.01)
- *B01F 13/00* (2006.01)
- *B01L 3/00* (2006.01)
- *G01N 35/10* (2006.01)
- *G01N 35/00* (2006.01)

(52) U.S. Cl.
CPC ........... *B01J 2219/00889* (2013.01); *B01J 2219/00891* (2013.01); *B01L 3/502738* (2013.01); *B01L 2200/027* (2013.01); *B01L 2200/028* (2013.01); *B01L 2300/0816* (2013.01); *B01L 2400/0487* (2013.01); *G01N 2035/00326* (2013.01)

(56) References Cited

U.S. PATENT DOCUMENTS

| | | | |
|---|---|---|---|
| 6,120,736 A * | 9/2000 | Ploug et al. | 422/81 |
| 6,495,103 B2 | 12/2002 | Hettinger | |
| 6,827,906 B1 | 12/2004 | Björnson et al. | |
| 2002/0124896 A1 | 9/2002 | O'Connor et al. | |
| 2004/0086872 A1 | 5/2004 | Childers et al. | |
| 2008/0071407 A1 * | 3/2008 | Schaffer et al. | 700/108 |
| 2010/0075425 A1 * | 3/2010 | Hofmann et al. | 422/68.1 |
| 2010/0099115 A1 * | 4/2010 | Mach et al. | 422/102 |

FOREIGN PATENT DOCUMENTS

| | | |
|---|---|---|
| DE | 20 2008 009 938 | 10/2008 |
| WO | WO 98/53300 | 11/1998 |
| WO | WO 2008/052758 | 5/2008 |

OTHER PUBLICATIONS

International Search Report of PCT/EP2010/003032 dated Sep. 16, 2010.

Jul. 14, 2014 Office Action for corresponding Chinese Patent Application No. 201080024515.5.

* cited by examiner

MODULAR FLOW INJECTION ANALYSIS SYSTEM

CROSS-REFERENCE TO RELATED APPLICATIONS

This application claims priority to International Application No. PCT/EP2010/003032 filed on May 18, 2010 and Application No. DE 20 2009 007 800.4 filed Jun. 4, 2009, the entire disclosures of which are hereby incorporated by reference.

The present invention relates to a modular flow injection analysis system which includes a sample connection, a reagent inflow and a media discharge.

In analytical chemistry, flow injection analysis (FIA) is known as an automated process for detecting specific substances in a sample and for determining their respective concentrations. Its fields of application include the clinical area and also environmental and pharmaceutical sectors. For example, flow injection analysis also allows drinking water to be monitored and examined.

Conventional devices for flow injection analysis and for segmented flow analysis (CFA—Continuous Flow Analysis), which operates similarly and in which individual sample sections are separated by air bubbles, consist of a distributor for providing and transporting the required reagents, an injection unit, a mixing unit, and a detection unit. These units are separate devices which are connected to one another by means of tubes. When individual units are exchanged for the purpose of adaptation to a different analysis task, these tube connections need to be separated and subsequently new connections need to be established again. On account of the permissible minimum radii of curvature of the tubes employed, the conventional flow injection analysis systems, with their individual units, require a large amount of space.

It is desirable to render the multitude of tube connections unnecessary and to achieve a smaller overall size and lower complexity in this way. The adjustment to different measurement tasks should be easy to realize without having to exchange the entire system and without having to establish new tube connections. At the same time, the analysis system should be expandable so that more complex, multistage problems can be solved.

The invention provides a modular flow injection analysis system which has a sample connection, a reagent inflow and a media discharge and is formed of a plurality of functional modules stacked one on top of the other. According to the features of claim 1, these functional modules include at least a metering module including a metering channel having an inlet and an outlet, a mixing module including a mixing channel having an inlet and an outlet, an analysis module including a media chamber connected to the outlet of the mixing channel, and a media control module. The modules are connected by aligned media channels. These media channels replace the conventional tube connections. They are connected automatically when the modules are fitted together.

A media control module selectively connects the sample connection or the reagent inflow to the inlet of the metering channel of the metering module by a valve control. Depending on the measurement task, this allows the desired reagent to be selectively injected into the sample, which could be drinking water, for example, with the length and cross-section of the metering channel determining the amount of the reagent supplied. Furthermore, the media control module is adapted to selectively connect the outlet of the metering channel to the inlet of the mixing channel or to a discharge by a valve control. To measure out a specific quantity of reagent, the metering channel is completely filled with the reagent. To this end, the media control module controls the reagent inflow to the inlet of the metering channel and connects the outlet of the metering channel to a reagent discharge for a period of time which ensures that the metering channel is completely filled with reagent. The metering channel permits a very precise metering even in case of a slightly varying flow rate and a coarser time control of the valve.

Preferably, the flow injection analysis system further comprises a media connection module which includes a sample connection and a waste connection. The sample that is mixed with the reagent flows off through the waste connection after the analysis has been effected in the analysis module.

In a preferred embodiment, the reagent inflow is provided in the media control module. The reagent inflow thus occurs in a different module from the sample connection. This is of advantage e.g. in laboratory environments in which the reagent reservoirs are arranged spatially separate from the sample reservoir and the length of the tube connections that are still necessary can be reduced by supplying the reagent from above and feeding the sample from below.

In a preferred embodiment, a sealing plate is inserted between the metering module and the mixing module, the sealing plate having passage openings for the media channels of the modules. One media channel is provided for the sample flow here, and one media channel connects the metering channel to the mixing channel.

The metering module is preferably in the form of a plate which has the metering channel recessed therein in a meander shape. The plate may be a cast part, for example. Since the quantities of reagent to be injected differ depending on the measurement task, the metering channel needs to be adjusted in terms of its holding capacity to the reagent to be injected. Therefore, different metering modules are preferably provided for the modular flow injection analysis system, which are interchangeable and have identical external dimensions and identical interfaces. They differ as regards the holding capacity of the metering channel, which can be achieved by different lengths and/or different cross-sections of the metering channel. The metering channel is preferably open to the top, which allows easy cleaning of the channel after disassembly of the individual modules. In the assembled form, the metering channel is closed e.g. by the media control module.

In a preferred embodiment, the mixing module is in the form of a plate which has the mixing channel recessed therein in a meander shape. The length of the mixing channel also depends on the measurement task. Some measurement tasks require a particularly long mixing channel. The mixing channel can be lengthened in that a mixing channel is recessed in a meander shape on both sides of the mixing module plate, the two mixing channel parts being connected to each other by means of a passage opening. Should, in view of the given external dimensions of the mixing module, the required length not yet be obtained by recessing a mixing channel on both sides of the plate, provision may be made for two mixing modules which are stacked on top of each other.

A sealing plate forms a cover of the mixing channel that is open to the top. This construction allows easy cleaning of the channel after a disassembly of the individual modules.

In a preferred embodiment, the media control module is provided with a 3/2-way valve which connects the inlet of the metering channel either with the sample connection or with the reagent connection. In a further embodiment, the media control module includes a further 3/2-way valve which connects the outlet of the metering channel either with the inlet of the mixing channel or with the discharge.

In one embodiment, the media chamber of the analysis module is traversed by at least one optical measuring path. This optical measuring path may be formed by a light source and an optical photodetector in a manner known per se. In flow injection analysis, the injection of a reagent generally causes a dispersion of the analyte which can be measured as a turbidity in the optical measuring path. A so-called concentration profile is measured; a peak progression develops that is known to a person of ordinary skill in the art.

In a preferred embodiment, the metering module is arranged adjacent to the media control module and the analysis module is arranged adjacent to the media connection module, and at least one media channel runs proceeding from the media connection module to the media control module and traverses all intermediate modules.

Preferably, the entirety of the modules stacked one on top of the other constitutes a cuboid or cube-shaped block.

In a preferred embodiment, the modules stacked one on top of the other have recesses which are aligned with each other and jointly form a receiving space. This receiving space may receive electronics, for example. Such electronics is adapted to drive the valves and/or the optical path, for example, and allows a connection to an external control unit. The electronics may also carry out a processing of the measuring signals obtained.

In a further embodiment, the flow injection analysis system may include a plurality of mixing modules arranged in series, which are provided with separate reagent connections. This allows different analysis tasks to be performed in one passage of the sample. Rather than the supply via a metering module, a different metering may also be made use of here for the reagent inflow, for example by means of a metering valve, a metering pump or by a double-T injection or similar metering methods.

Preferably, provision is made for an additional connection module which is arranged downstream in series with a mixing module and establishes a media connection to a separate module block. This allows a flow injection analysis system to be produced from a plurality of separate module blocks for complex analysis tasks. Here, the separate module block preferably includes a further mixing module and a further analysis module.

Further advantages and configurations of the invention will become apparent from the description below of a preferred embodiment, given with reference to the drawing figures, in which.

Figure 1:
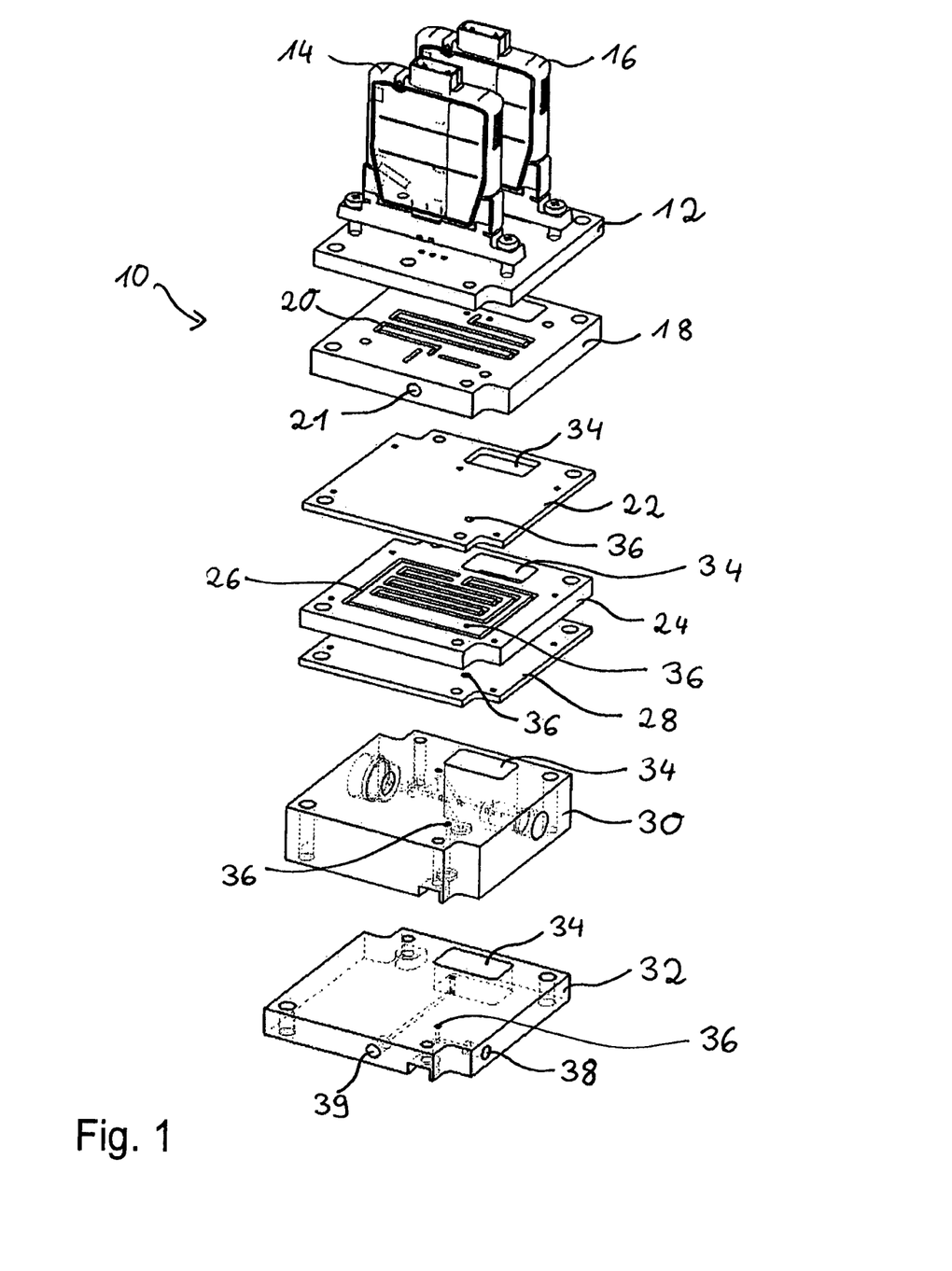
FIG. 1 shows a complete module block in a schematic exploded view.

FIG. 1 shows an exploded view of a module block 10 according to the invention, with one possible composition of a plurality of functional modules. A media control module 12 comprises a first 3/2-way valve 14 and a second 3/2-way valve 16. The media control module 12 has a reagent connection (not shown) for supplying a reagent.

An underlying metering module 18 has a meander-shaped metering channel 20 and an outflow connection 21 for the reagent. A sealing plate 22 is disposed below the metering module 18. An underlying mixing module 24 includes a likewise meander-shaped mixing channel 26.

A sealing plate 28 is disposed under the mixing module 24. The sealing plate 28 is adjoined by an analysis module 30 having a media chamber (not shown). In the embodiment illustrated in FIG. 1, the module block 10 is terminated by a media connection module 32.

All functional modules from which the module block 10 is assembled and also the two sealing plates contained have approximately the same external dimensions in width and length. The modules are substantially plate-shaped and have different heights, adapted to their respective tasks. In the assembled state, a cuboid module block or, depending on the height of the modules, a cube-shaped module block is produced. The material from which the modules are made is selected such that it fulfills the requirements of the analysis task, i.e. is resistant, for example, to the sample fluid and to the reagent or reagents. A detachable surface seal with corresponding recesses at the media transfer points may be provided between the individual modules, or the seal is realized by means of a joining technique.

All of the modules and sealing plates each include a recess 34 in alignment with each other and jointly defining a receiving space. This receiving space may accommodate electronics, for example.

Likewise visible in FIG. 1 are passage openings 36 on the media connection module 32, the analysis module 30, the sealing plates 22 and 28, and the mixing module 24, which are all in alignment with each other to define a continuous media channel. This media channel is connected to a sample connection 38 on a side surface of the media connection module 32, the sample fluid being supplied through the sample connection in the exemplary embodiment shown. The media connection module 32 further includes a waste connection 39 for connection to a waste container (not shown).

Figure 2:
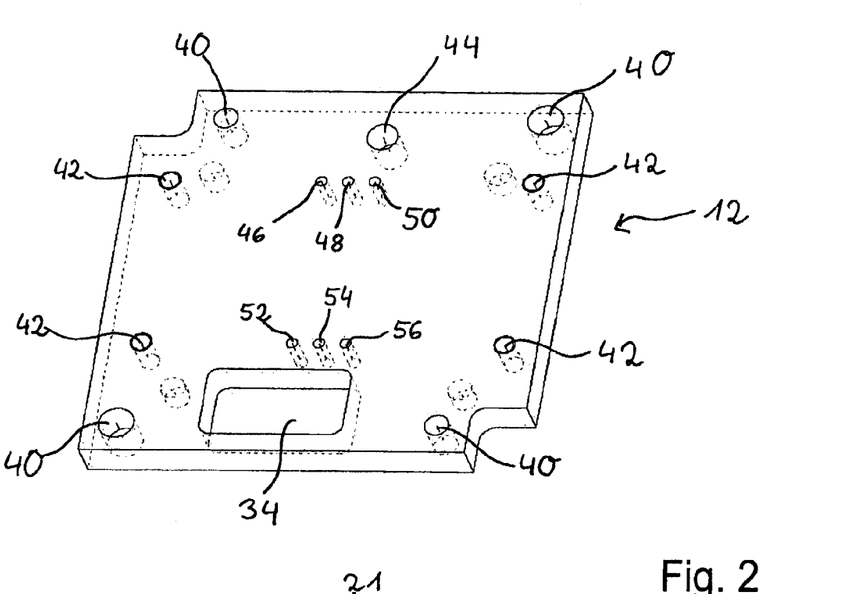
FIG. 2 shows a media control module.

FIG. 2 shows the media control module 12 without the 3/2-way valves 14 and 16 put on. As already discussed in connection with FIG. 1, the recess 34 defines a receiving space together with the recesses in the other modules. Boreholes 40 serve to receive fastening means for connecting the individual functional modules to form a module block. It is, of course, also conceivable to connect the modules to one another using other means. Boreholes 42 serve to attach the valves 14 and 16.

The media control module 12 includes a reagent connection 44 at which the reagent can be supplied via a reagent line. Passage openings 46, 48 and 50 are connected to the 3/2-way valve 14 which selectively allows a connection of the passage openings 46 and 48 or of the passage openings 48 and 50. The passage opening 46 is aligned with the passage openings denoted by 36 in FIG. 1, which together define a media channel through which the sample fluid is directed from the media connection module 32 to the media control module 12. The passage opening 48 defines a fluidic connection to the inlet of the underlying metering channel 20 in the metering module 18. The reagent connection 44 is in fluid communication with the passage opening 50 via a reagent inflow in the metering module.

The 3/2-way valve 16 controls the connection between passage openings 52, 54 and 56 so as to selectively allow a connection of the passage openings 52 and 54 or of the passage openings 54 and 56. Passage opening 52 defines a fluidic connection to a reagent discharge in the metering module 18; passage opening 54 defines a fluidic connection to the outlet of the metering channel 20 while passage opening 56 defines a fluidic connection to the inlet of the mixing channel 26 in the mixing module 24.

Figure 3:
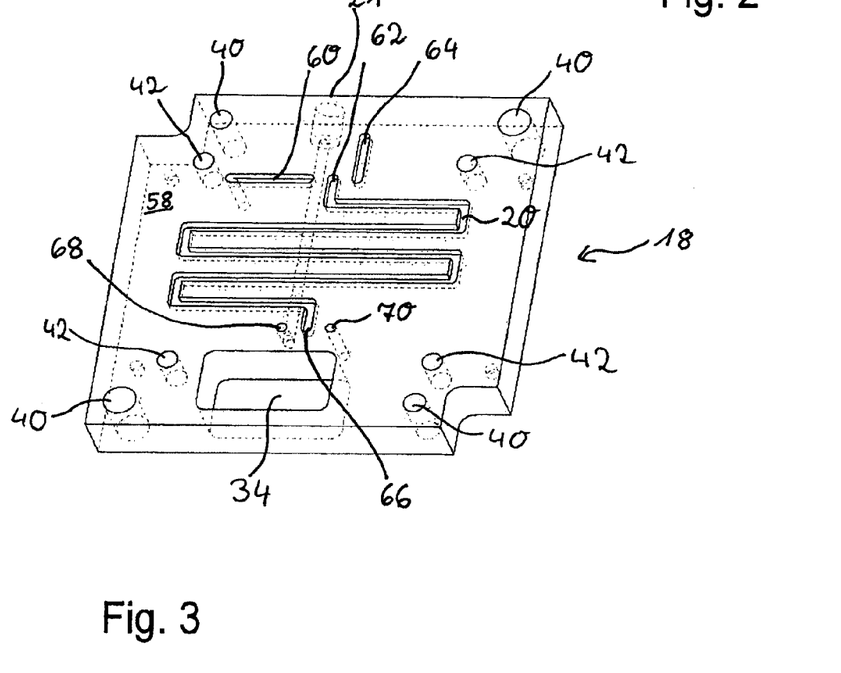
FIG. 3 shows a metering module.

FIG. 3 shows the metering module 18 which lies under the media control module 12 and is in the form of a plate 58. Again, boreholes 40 serve to receive fastening means and, as with the media control module 12, boreholes 42 serve to attach the valves 14 and 16. The media control module 12 and the metering module 18 together constitute an injection module. The metering channel 20 is open toward the media control module 12 and is delimited toward the top by the latter. In the disassembled condition, the metering channel 20 is therefore freely accessible and can be easily cleaned. In the present embodiment, the metering channel 20 is recessed in a meandering shape in the plate 58. In other configurations of the metering module 18, the metering channel 20 may be led through the metering module over the shortest possible distance. When a lengthening of the metering channel and, hence, an enlargement of the reagent volume is desired, the metering channel may be guided in a larger number of loops, or its cross-section may be increased. Depending on the requirement, the module block 10 may thus be fitted with different metering modules.

A sample inflow 60 is in fluid communication with the passage opening 46 of the media control module 12. An inlet 62 of the metering channel 20 is in fluid communication with the passage opening 48 of the media control module 12. A reagent inflow 64 is in fluid communication with the passage opening 50 of the media control module 12. By means of the valve 14, either the sample inflow 60 or the reagent inflow 64 can be connected with the inlet 62 of the metering channel 20.

An outlet 66 of the metering channel 20 is in fluid communication with the passage opening 54 of the media control module 12. A reagent discharge 68 is in fluid communication with the passage opening 52 of the media control module 12 and provides a passage to the outflow connection 21 for the reagent, which is not visible in FIG. 3. A passage opening 70 is in fluid communication with the passage opening 56 of the media control module 12 and provides a passage to the inlet of the mixing channel 26 in the mixing module 24.

Figure 4:
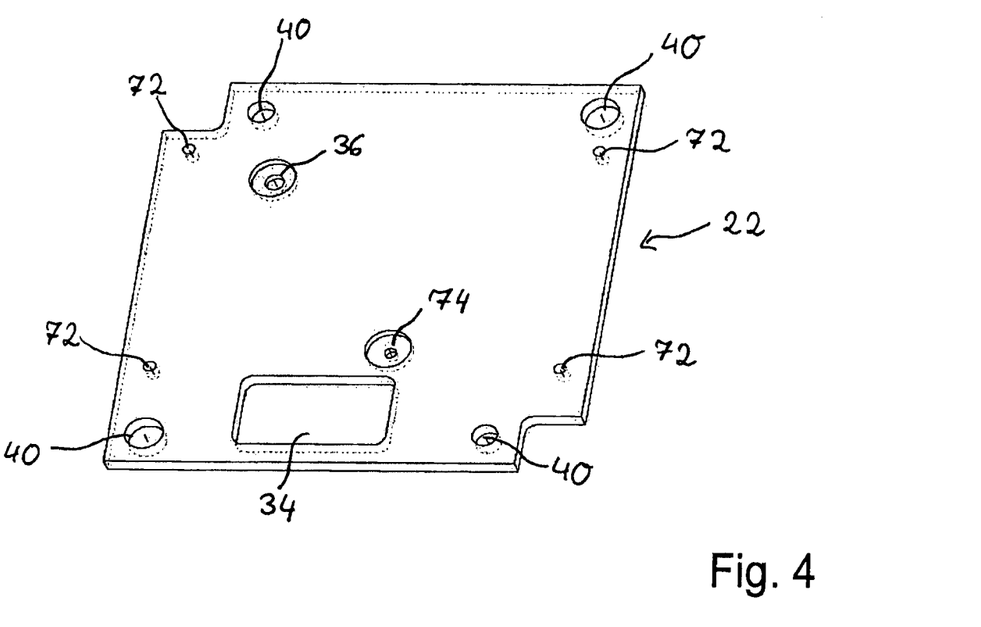
FIG. 4 shows a sealing plate.

FIG. 4 shows the sealing plate 22 which again has boreholes 40 to receive fastening means that hold the entire module block together. The sealing plate 22 further has boreholes 72 that serve to receive fastening means for holding the sealing plate 22 and the underlying mixing module 24 and, if required, a further sealing plate 28 located under the mixing module 24 together. The sealing plate 22 of course also features the recess 34 to form a receiving space. The sealing plate has the function of delimiting toward the top the underlying mixing channel or mixing section 26 that is recessed in the mixing module. A passage opening 74 is in fluid communication with the passage opening 70 of the metering module 18 and defines a passage to the inlet of the mixing section 26. The passage opening 36 is in fluid communication with the sample inflow 60 and, together with further passage openings 36 in underlying modules, defines a media channel to the sample connection 38, as already discussed with reference to FIG. 1.

Figure 5:
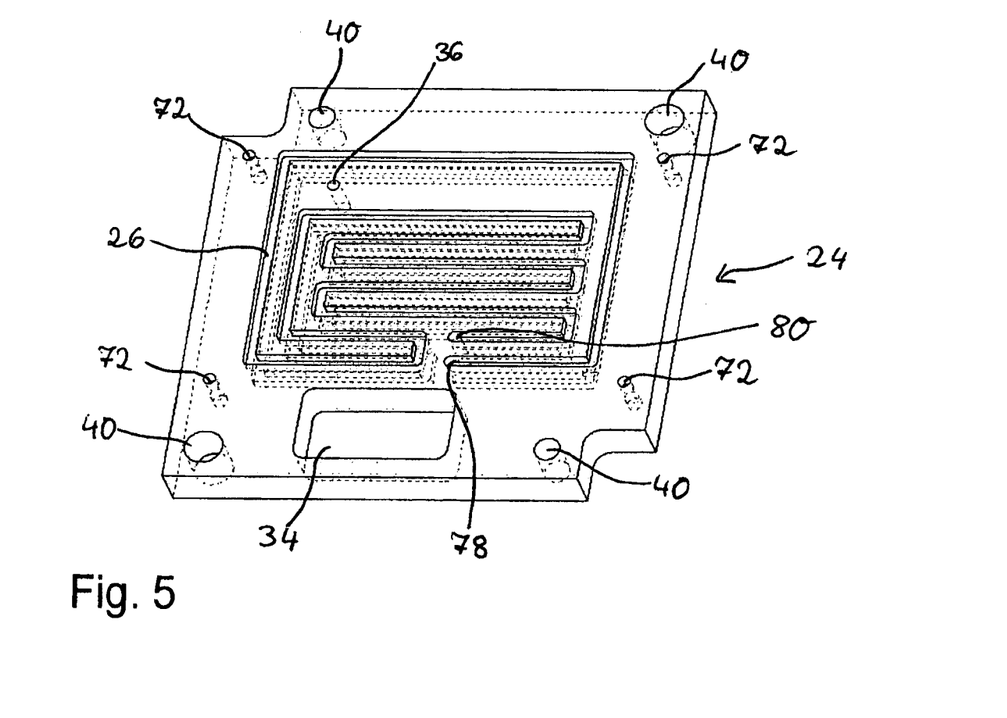
FIG. 5 shows a mixing module.

The mixing module 24 illustrated in FIG. 5 is formed by a plate which has the mixing channel 26 recessed therein. The mixing module 24 further again includes a recess 34 as well as boreholes 40 and boreholes 72 which serve for attachment purposes, as already set forth.

Similar to the metering channel 20, the mixing channel 26 is of a meander-shaped design. The length of the mixing channel may be varied by having the channel run in a larger or smaller number of loops. If the length of the mixing channel 26 that can be obtained in this way is not sufficient for the intended analysis purpose, a mixing channel may also be recessed on the opposite side of the mixing module.

An inlet 78 of the mixing channel 26 is in fluid communication with the passage opening 74 in the sealing plate 22. An outlet 80 of the mixing channel 26 is in fluid communication with an input of the underlying analysis module 30 if the length of the mixing channel 26 on only one side of the plate is sufficient. When a longer mixing section is needed, the outlet 80 of the mixing channel 26 on the illustrated side of the mixing module 24 leads to a second part of the mixing channel 26 which is recessed on the rear side of the plate. The outlet of the mixing channel 26 on the opposite side is then in fluid communication with the inlet of the analysis module 30. That is, the two parts of the mixing channel 26 are connected in series.

In case the mixing module 26 includes a mixing channel on the rear side as well, a second sealing plate 28 is provided that delimits the mixing channel. For analysis tasks requiring a mixing section that is not realizable on the two sides of a mixing module plate when the external dimensions as provided of the mixing module are taken as a basis, two mixing modules may be placed on top of each other, which are separated by a sealing plate. The second mixing module may then in turn feature a channel on only one side or else may have channels on both sides, as required. This allows the module block to be expanded for a variety of analysis purposes while the width and length dimensions remain unchanged.

The mixing module 24 further likewise includes a passage opening 36 which is in fluid communication with the passage opening 36 of the sealing plate 22 and defines a media channel to the sample connection 38.

Figure 6:
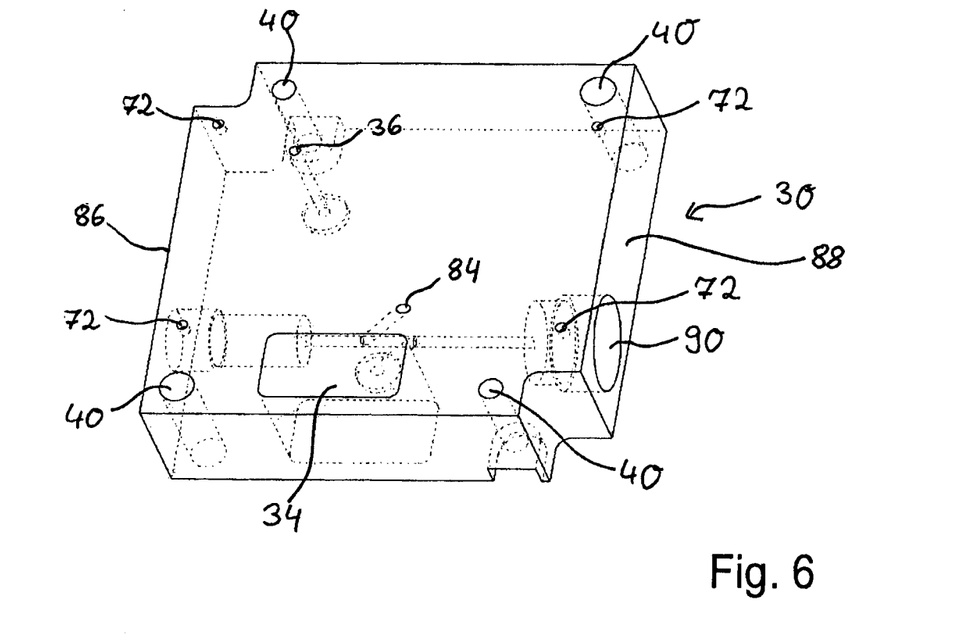
FIG. 6 shows an analysis module.

FIG. 6 shows the analysis module 30 having a recess 34, boreholes 40 and boreholes 72. An inlet 84 is in fluid communication with the outlet 80 of the mixing channel 26 in the mixing module 24. The fluid that is caused to flow through the mixing module 26 flows through the inlet 84 and reaches a medium chamber (not illustrated) of the analysis module 30. The media chamber is traversed by an optical measuring path. To this end, a light source which may be formed by an LED, for example, is disposed at a narrow side 86 of the analysis module 30. A photodetector 90 is arranged on an opposite narrow side 88 of the analysis module 30. The optical measuring path is located between the light source and the photodetector. In flow injection analysis, the reagent reacts with the sample in such a way that a turbidity or change in color occurs. This causes a change in the optical properties of the medium that is present in the optical measuring path, and a peak progression, well known to a person of ordinary skill in the art, in the signal received by the photodetector is the result.

Depending on the measurement task, the modular flow injection analysis system may also be equipped with a different analysis module. For example, the analysis module may also include electrochemical sensors, conductivity sensors or other sensors commonly used in analyses.

Other processes for sample conditioning or other method steps such as extraction, gas diffusion cells or dialysis cells may also be embedded as separate modules.

A passage opening 36 is again in fluid communication with the passage opening 36 in the mixing module 24 and is part of the media channel to the sample connection 38.

Figure 7:
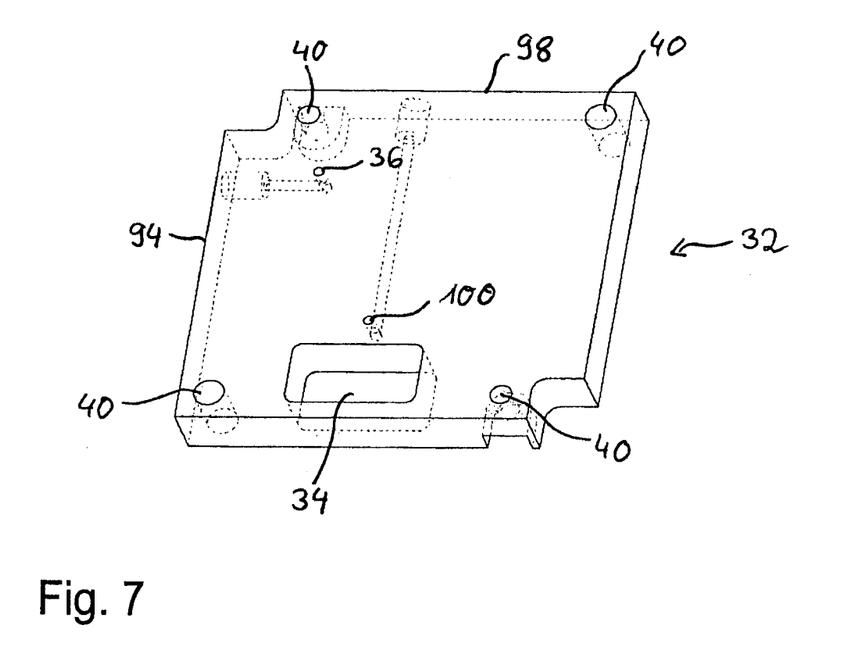
FIG. 7 shows a media connection module.

FIG. 7 shows the media connection module 32, which likewise includes boreholes 40 and a recess 34. The sample connection 38 (not visible in FIG. 7) for the sample fluid is provided on a side surface 94. The sample connection 38 is in fluid communication with a passage opening 36 which in turn is in fluid communication with the passage opening 36 in the analysis module 30.

The media discharge 39 (also not visible in FIG. 7) for a connection to a waste container is provided on a side surface 98. The sample connection and the media discharge could, of course, also be provided on a different side surface or else on the rear side. The arrangement on side surfaces has the advantage that the module block 10 with the media connection module 32 can be installed on a flat surface and the inflows and outflows occur at the sides. It is also possible to do without a media connection module altogether and to provide the sample connection in the injection module, for example, and the media discharge in the analysis module, for example.

A passage opening 100 is in fluid communication with an outlet of the media chamber of the analysis module 30 and, inside the media connection module 32, in fluid communication with the media discharge 39.

In operation, the separately discussed modules, that is, the media control module 12, the metering module 18, the sealing plate 22, the mixing module 24, along with a sealing plate 28, if required, the analysis module 30, and the media connection module 32, are stacked one on top of the other, and fastening means are inserted through the aligned boreholes 40 to hold the stack of modules together as a module block 10.

Beforehand, the sealing plates 22 and 28 and also the mixing module 24 and the analysis module 30 may be additionally connected to each other one below the other by means of fastening means using the aligned boreholes 72. The recesses 34 are likewise in alignment and together define a receiving space for insertion of an electronics assembly therein which is utilized, e.g., to control the module block 10 and for analysis evaluation. The control electronics may also provide a connection to a superordinate control unit. A connection to the Internet is also feasible, which allows the analysis evaluation to be effected on-line at another place.

The modules stacked on top of each other have substantially cube-shaped dimensions in this configuration, i.e. the module block 10 has the same width, length and height, with the valves 14 and 16 placed on top not included. The handy module block 10 can be placed on a surface, with the sample to be examined—drinking water in the present example—being supplied from the side via a connection in the media connection module 32 by means of a tube. The sample traverses the entire module block 10, proceeding from the sample connection 38 via the media channel defined by the passage openings 36 in the analysis module 30, in the sealing plate 28, in the mixing module 24 and in the sealing plate 22 to the sample inflow 60 in the metering module 18. The reagent is conducted into the reagent inflow 64 from above via the reagent connection 44 in the media control module 12.

A measurement first starts, for example, with a reference measurement without an injected reagent. To this end, the valve 14 switches the sample inflow 60 to the inlet 62 of the metering channel 20, and the valve 16 switches the metering channel outlet 66 to the passage opening 70 which is in fluid communication with the inlet 78 of the mixing channel 26. The sample is conveyed into the module block 10 by means of a pump not contained in the module block 10 or by means of an admission pressure. In doing so, as constant a flow rate as possible is to be maintained. The sample flows via the metering channel 20 into the mixing channel 26 and via the outlet of the mixing channel into the media chamber of the analysis module 30. Only the sample is then present in the photo path between the light source and the photodetector 90 and a reference measurement can be carried out. The sample leaves the media chamber in the analysis module 30 and flows in the media connection module 32 from the passage opening 100 to the media discharge 39 in the side wall 98 and then into the waste container. The sample thus traverses the entire module block from top to bottom as well through a second media channel formed from the metering channel, the mixing channel and the media chamber and the respective passage openings located in between.

To inject a reagent, the valve 14 and the valve 16 are switched, so that the reagent inflow 64 is connected to the inlet 62 of the metering channel 20 and the outlet 66 of the metering channel 20 is connected to the reagent discharge 68 which is in fluid communication with the outflow connection 21 for the reagent.

Using a pump, for example, the reagent is conducted into the metering channel 20 until the latter is completely rinsed. The injection quantity is defined here by means of the metering channel length and the metering channel cross-section. To ensure that the metering channel 20 is rinsed completely, excess reagent is conducted via the reagent discharge 68 to the outflow connection 21 and from there out of the module block 10.

Subsequently, the valves 14 and 16 are both switched, causing the sample to be applied to the metering channel inlet 62 again, and the metering channel outlet 66 is connected to the inlet 70 of the mixing channel 26. The sample washes the reagent through the mixing section or the mixing channel 26 into the media chamber of the analysis module 30 which, with its optical measuring path, constitutes a flow photometer in the example illustrated. Here the extinction is determined in a time-dependent manner. The measurement evaluation produces the typical peak profile which can also be evaluated automatically in accordance with the usual methods of flow injection analysis. The sample and the reagent leave the module block 10 via the media discharge 39 in the media connection module 32.

The flow injection analysis system may be operated as an on-line analysis apparatus, with the drive causing samples to be taken from a reservoir by an interval control and to be analyzed automatically. The removal may be realized by means of a sampling unit. But the analysis may also occur individually for each sample (e.g. autosampler) and for this purpose, pumping is effected from a vessel. The module block 10 allows both the flow injection analysis and the so-called inverse (reversed) flow injection analysis. In the first-mentioned case, a reagent is injected into the sample, the sample forming the so-called carrier stream; in the latter case, the sample is injected into the reagent, the reagent forming the so-called carrier stream. To this end, the reagent therefore needs to be fed at the sample connection 38 and the sample needs to be fed at the reagent connection 44. Otherwise, the process remains as described.

Figure 8:
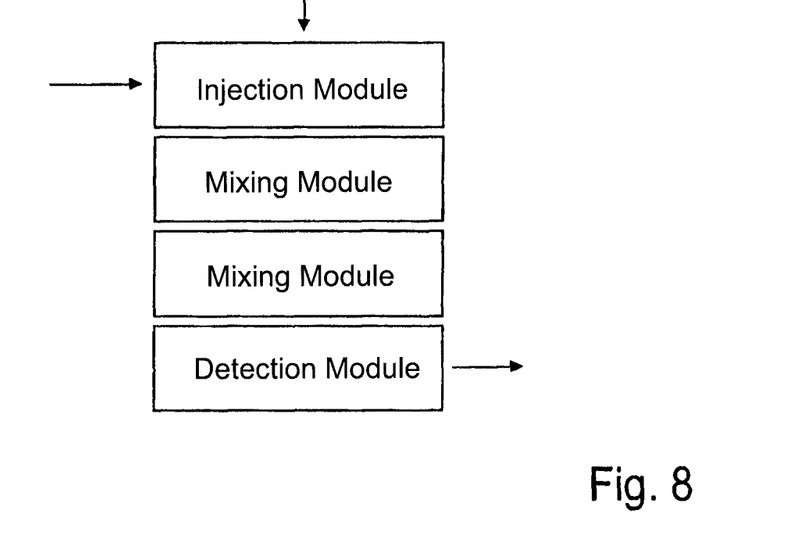
FIGS. 8 to 10 schematically show various compositions of the modular flow injection analysis system from different modules.

FIG. 8 shows purely schematically a further possible combination of functional modules in a module block. An injection module, consisting of the media control module with valves placed on and the metering module, has two connections, one for the inflow of the reagent and one for the inflow of the sample, with the reagent or the sample serving as the carrier stream. As described in FIGS. 1 to 7, the carrier stream may be fed at the bottom in the module block. But provision is also made for an embodiment in which a connection for the carrier stream is provided on the media control module.

The structure according to FIG. 8 contains two mixing modules to form a particularly long mixing section. The two mixing modules preferably each contain a mixing channel on the upper and on the lower side and are stacked on top of each other. The lowermost module is a detection module which may be assembled from an analysis module 30 and a media connection module 32. After the analysis the sample and the reagent are conveyed to a waste container.

Figure 9:
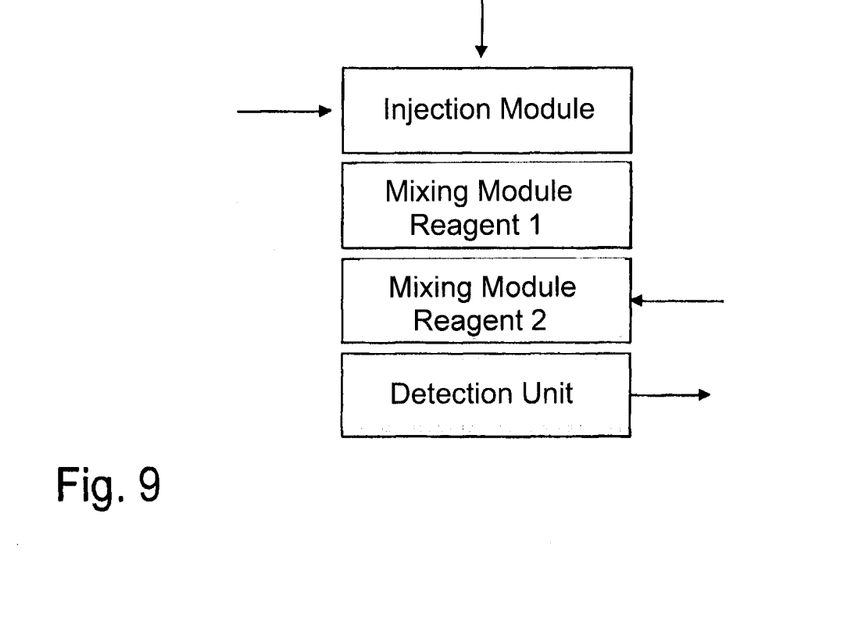

FIG. 9 shows purely schematically an example of a construction of a module block 10 for a procedure operating with a plurality of reagents. Again, the topmost module is an injection module consisting of a media control module with two valves and a metering module. The feeding of the reagent and of the sample in the injection module is also indicated in this schematic example. Again, a mixing module is situated underneath it, in which the sample and the reagent 1 are brought together in a mixing section. The first mixing module is followed by a second mixing module having a second mixing channel. In this case, this second mixing module is not a lengthening of the mixing section, but a second reagent is supplied to this mixing module from outside. This reagent may be supplied actively by means of a metering pump or a metering valve. The actual analysis is effected in the detection unit located thereunder. The detection unit, for its part, is provided with a connection to the waste container for discharging the sample and the reagents 1 and 2.

If the overall height provided is limited, for example, or if available modules are to be employed in a new combination, a further embodiment consists in constructing the flow injection analysis system from a plurality of module blocks. A connection module is provided here which is arranged downstream in series with a mixing module and establishes a media connection to a separate module block.

Figure 10:
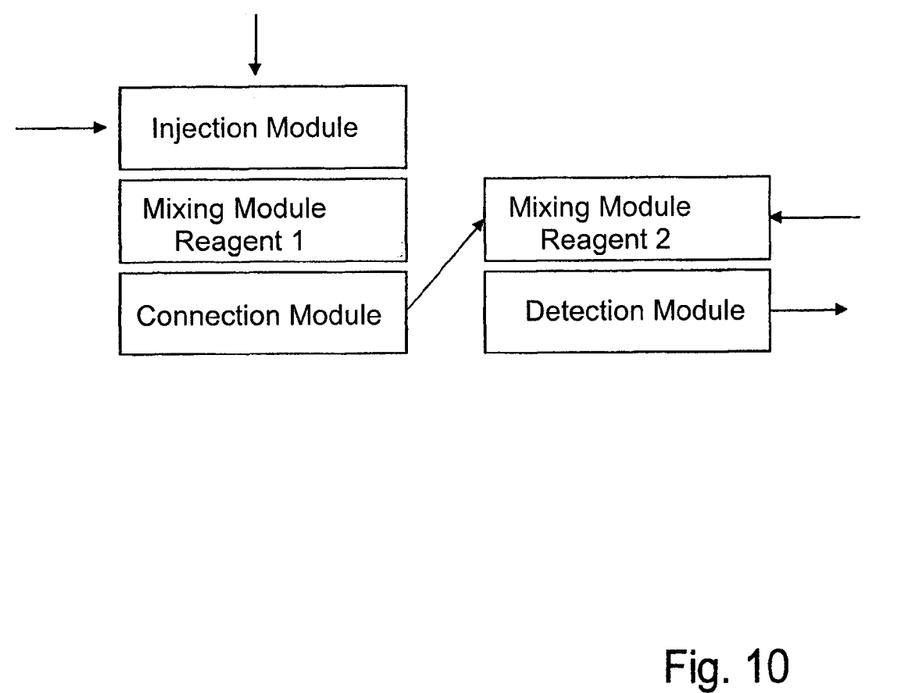

FIG. 10 again shows an injection module in a known manner, which is supplied with a first reagent, for example as a carrier stream, and a sample. The sample and the reagent 1 are brought together in a mixing module arranged thereunder. As opposed to the illustration in FIG. 9, the mixing module with the reagent 1 is not stacked on a further mixing module with the reagent 2, but a connection module is disposed as the lowermost module in module block 1. The connection module has a connection to the outside for connection to a tube. This tube provides a media connection to an inlet connection of a second mixing module to which a reagent 2 is supplied. This mixing module with the reagent 2 is mounted on a detection module which, like in FIG. 9, carries out the analysis of the two reagent reactions and has a connection to the outside to the waste container. The difference between FIGS. 9 and 10 merely resides in the separate construction, which allows not to exceed a specified overall height.

The invention claimed is:

1. A modular flow injection analysis system comprising a sample inflow, a reagent inflow and a media discharge, formed of a plurality of functional modules which are stacked one on top of the other and at least include:
   a) a metering module including a metering channel having an inlet and an outlet;
   b) a mixing module including a mixing channel having an inlet and an outlet;
   c) an analysis module including a media chamber connected to the outlet of the mixing channel;
   d) a media control module;
   characterized in that:
      the metering channel having a length and a cross-section determining the amount of the reagent supplied;
      the modules have passage openings which are all in alignment with each other to define a continuous media channel by which the modules are connected and the media channel is connected to a sample connection;
      the media control module selectively connects one of the sample inflow and the reagent inflow to the inlet of the metering channel of the metering module by a valve control;
      the media control module selectively connects the outlet of the metering channel to one of the inlet of the mixing channel and a reagent discharge by a valve control; and
      the media control module operable to measure out a specific quantity of reagent by controlling the reagent inflow to the inlet of the metering channel and connecting the outlet of the metering channel to the reagent discharge for a period of time to ensure that the metering channel is completely filled with the reagent.

2. The modular flow injection analysis system according to claim 1, further comprising a media connection module which includes the sample connection and the media discharge.

3. The modular flow injection analysis system according to claim 1, wherein the media control module includes a reagent connection.

4. The modular flow injection analysis system according to claim 1, wherein a sealing plate is inserted between the metering module and the mixing module, the sealing plate having passage openings for the media channels of the modules.

5. The modular flow injection analysis system according to claim 1, wherein the metering module is in the form of a plate which has the metering channel recessed therein in a meander shape.

6. The modular flow injection analysis system according to claim 1, wherein the mixing module is in the form of a plate which has the mixing channel recessed therein in a meander shape.

7. The modular flow injection analysis system according to claim 1, wherein a sealing plate is inserted between the mixing module and the analysis module, the sealing plate having passage openings for the media channels of the modules.

8. The modular flow injection analysis system according to any of the preceding claims, wherein the media control module includes a 3/2-way valve which connects the inlet of the metering channel with one of the sample inflow and the reagent inflow.

9. The modular flow injection analysis system according to claim 1, wherein the media control module includes a 3/2-way valve which connects the outlet of the metering channel with one of the inlet of the mixing channel and the reagent discharge.

10. The modular flow injection analysis system according to claim 1, wherein the media chamber of the analysis module is traversed by at least one of an optical, electrochemical and physical measuring path.

11. The modular flow injection analysis system according to claim 2, wherein the metering module is arranged adjacent to the media control module and the analysis module is arranged adjacent to the media connection module, at least one media channel being guided proceeding from the media connection module to the media control module and traversing all intermediate modules.

12. The modular flow injection analysis system according to claim 1, wherein the entirety of the modules stacked one on top of the other constitutes a cuboid or cube-shaped block.

13. The modular flow injection analysis system according to claim 1, wherein the modules stacked one on top of the other have recesses which are aligned with each other and jointly form a receiving space.

14. The modular flow injection analysis system according to claim 1, wherein the reagent connection and the sample connection are interchangeable as required.

15. The modular flow injection analysis system according to claim 1, wherein a plurality of mixing modules is arranged in series and provided with separate reagent connections.

16. The modular flow injection analysis system according to claim 1, comprising an additional connection module which is arranged downstream in series with a mixing module and establishes a media connection to a separate module block.

17. The modular flow injection analysis system according to claim 16, wherein the separate module block includes a further mixing module and an analysis module.

18. The modular flow injection analysis system according to claim 2, wherein the media control module includes a reagent connection.

* * * * *